United States Patent [19]

Zoeller

[11] Patent Number: 4,788,341

[45] Date of Patent: Nov. 29, 1988

[54] PROCESS FOR PREPARING 2-ACETONAPHTHONES

[75] Inventor: Joseph R. Zoeller, Kingsport, Tenn.

[73] Assignee: Eastman Kodak Company, Rochester, N.Y.

[21] Appl. No.: 107,745

[22] Filed: Oct. 13, 1987

[51] Int. Cl.$^4$ ............................................. C07C 45/45
[52] U.S. Cl. ..................................... 568/315; 568/42; 560/57; 560/139; 562/462
[58] Field of Search .................... 568/312, 315, 42; 560/57, 139; 562/462

[56] References Cited

U.S. PATENT DOCUMENTS

| | | | |
|---|---|---|---|
| 3,592,826 | 7/1971 | Marcus et al. | 568/312 |
| 3,708,540 | 1/1973 | Yokotani et al. | 568/315 |
| 4,287,367 | 9/1981 | Kuesters et al. | 568/315 |
| 4,593,125 | 6/1986 | Davenport et al. | 568/319 |

FOREIGN PATENT DOCUMENTS

| | | | |
|---|---|---|---|
| 3531982 | 3/1986 | Fed. Rep. of Germany | 568/319 |
| 3518668 | 11/1986 | Fed. Rep. of Germany | 568/319 |
| 3519009 | 11/1986 | Fed. Rep. of Germany | 568/319 |
| 2164337 | 3/1986 | United Kingdom | 568/319 |

OTHER PUBLICATIONS

Canevet et al, Chem. Abst., vol. 80, #82315v (1974).
Calmon et al, Chem. Abst., vol. 76, #126217p (1972).
Gasparrini et al, Tetrahedron, 40:1491 (1984).
Jones, Org. Reactions, 15:204 (1967).
Dinulescu et al, Tetrahedron, Supplement 1:37:55 (1981).
Vebrel et al, Bull. Chim. Soc. Fr., Part II:116 (1982).
Ito et al, J. Org. Chem., 39:2769 (1974).
Myrboh et al, J. Org. Chem., 48:5327 (1983).
Hyatt et al, J. Org. Chem., 49:384 (1984).

Primary Examiner—James H. Reamer
Attorney, Agent, or Firm—Charles R. Martin; William P. Heath, Jr.

[57] ABSTRACT

2-Acetonaphthones are prepared by heating a compound selected from the group consisting of ketals and enol ethers of acetyl-substituted benzalacetone at a temperature effective to cyclize the compound and form said 2-acetonaphthones.

18 Claims, No Drawings

PROCESS FOR PREPARING 2-ACETONAPHTHONES

BACKGROUND OF THE INVENTION

1. Field of the Invention

The present invention relates to a novel process for preparing 2-acetonaphthones by cyclizing a ketal or acyl-substituted benzalacetones.

2. Description of the Prior Art

2-Acetonaphtones are very useful as drug intermediates. Heretofore, 2-acetonaphthones have been prepared by processes described in the forementioned references and in U.S. Pat. No. 4,593,125 and J. A. Hyatt and P. W. Raynolds, J. Org. Chem., 49, 384 (1984) and German Pat. Nos. 3,519,009 and 3,518,668. The present invention provides an alternative, more expedient, and economical route for the preparation of these compounds.

Substituted 2-acetonaphthones are also useful as polymer intermediates in the chemical industry, particularly for the preparation of substituted 2-naphthanoic acids and esters thereof. However, the methodology for making 2-naphthanoic acids and esters thereof is very sparse. The major problem posed by the synthesis of these compounds is that, for the 2-naphthanoic acid derivatives to be useful as polymer intermediates, a second functional group besides the carboxyl group must be present. Moreover, such a functional group must be present at a specific location on the molecule. Thus, a single, specific isomer of a substituted 2-naphthanoic acid or ester thereof must be produced out of a large number of distinguishable isomeric naphthanoic acids. The development of such a process is, therefore, of great significance to the industry.

Specific 2-naphthanoic acids have been synthesized by the prior art. For example, see U.S. Pat. Nos. 4,594,445; 4,506,092; and 4,486,605. However, none of these methods are applicable to the general class of 2-naphthanoic acids or esters synthesized by the process of this invention.

Thus, there is still a need for a simple and general process for the synthesis of 2-naphthanoic acids and esters thereof having a predictable substitution pattern. The present invention enables such a synthesis through the preparation of substituted and unsubstituted 2-acetonaphthones which can be oxidized by conventional methods to the 2-naphthanoic acids or esters thereof.

SUMMARY OF THE INVENTION

This invention relates to a process for preparing a 2-acetonaphthones of the formula

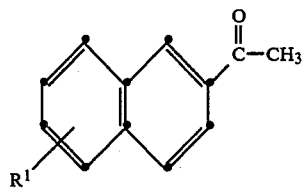

wherein $R^1$ is H, halo or $(C_1-C_{12})$alkoxy, acyloxy, carboxy, carbalkoxy, acyl, alkyl or thioalkyl, said process comprising heating a compound selected from the group consisting of a ketal of the formula

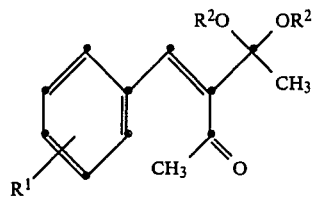

wherein $R^1$ is described above, and each $R^2$ is $(C_1-C_{12})$alkyl or the two $R^2$ taken together are $(C_2-C_{12})$alkylene, and an enol ether of the formula

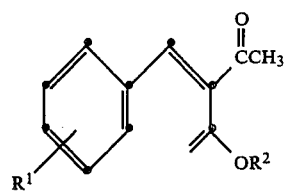

wherein $R^1$ is as defined above and $R^2$ is $(C_1-C_{12})$alkyl or acyl at a temperature effective to cyclize the compound and obtain said 2-acetonaphthones.

This invention also relates to a process for preparing a 2-acetonaphthones which comprises reacting an acyl-substituted benzalacetone of the general formula

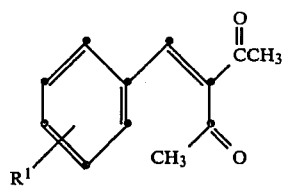

wherein $R^1$ is as defined above, with a ketalizing agent selected from the group consisting of alkyl glycols and tri-alkyl orthoesters and preformed dialkyl ketals and acetals; said benzalacetone and said ketalizing agent being present in a proportion and under conditions effective to form a compound selected from the group consisting of a ketal of the formula defined above; and an enol-ether of the formula defined above and heating the thus obtained compound at a temperature effective to cyclize the compound and form said 2-acetonaphthones.

In addition, this invention also relates to a process for preparing 2-acetonaphthones by reacting a diketone such as acetylacetone with a benzaldehyde substituted with H, halo or $(C_1-C_{12})$alkyl, carboxy, carbalkoxy, acyloxy, acyl, alkoxy or alkylthio; said diketone and said benzaldehyde being present in a proportion and under conditions effective to produce an acyl-substituted benzalacetone of the formula defined above; reacting the acyl-substituted benzalacetone with a ketalizing agent selected from the group consisting of alkyl glycols and tri-alkyl orthoesters and preformed dialkyl acetal or ketals, said ketalizing agent being present in proportion and under conditions effective to produce a compound selected from the group consisting of a ketal and an enol-ether of the benzalacetone of the formula defined above; and heating the thus obtained compound at a temperature effective to cyclize said compound and form said 2-acetonaphthones.

A more complete appreciation of the invention and many of the attendant advantages thereof will be readily perceived as the same becomes better understood by reference to the following detailed description of the preferred embodiments thereof.

DESCRIPTION OF THE PREFERRED EMBODIMENTS

The process of the invention for preparing a 2-acetonaphthones, the ketal or the enol-ether thereof relies on a thermal ring closure of the latter. The cyclization may be performed either in the liquid or vapor phases, with the latter being generally preferred since it can be conducted even in the absence of a solvent and produces generally higher yields of product.

When the cyclization is conducted in the vapor phase, it is done at a temperature of about 150° to 800° C., and more preferably about 350° to 600° C., and a pressure of about 0.001 mmHg to 3 atm, and preferably about 0.1 mmHg to atmospheric pressure. However, much higher temperatures can also be used without difficulty such as temperatures in excess of about 800° C. These temperatures are easily attainable in an industrial environment.

More commonly, the vapor phase cyclization reaction is conducted at ambient pressure using an inert gas purge to promote the transport of materials across a pyrolysis chamber. However, any feasible pressure below atmospheric pressure may suitably be employed and actually serves to promote the vaporization of the starting acids or esters. By means of example, a pressure of about 10 mmHg can be attained in an industrial environment. Higher pressures than those described above may also be employed, particularly in the case where the starting acids or esters are volatile. However, due to the need to vaporize the starting material the pressure is practically limited to about several atmospheres.

With the vapor phase reaction, the temperature of pyrolysis should be sufficiently high to allow the reaction to proceed at a reasonable rate and attain good conversion rates. The temperature should also be sufficient to completely vaporize the ketal or enol ether of the acyl-substituted benzalacetone. In most cases, this is accomplished by using a reactor temperature of about 470° to 530° C. Except when operating under high vacuum, these temperatures lead to reaction products in which all of the ketal or enol ether of the benzalacetone has been consumed. The best conditions are those that favor rapid vaporization. Thus, the lowest possible pressure should be employed. Industrially, this implies pressures of about 10 mmHg to 60 mmHg since these are generally regarded as the lowest pressures which are economically attainable. However, in the case of more highly valued products, even lower pressures may be used to some advantage. Higher pressures than those described above may also be employed, particularly in the case where the starting ketal of enol ether is volatile. At temperatures below 470° C., the ketal or the related enol ether of the benzalacetone are about 60% to 70% consumed. Thus, significantly lower temperatures are suitable, particularly if the starting materials are recycled to increase the yield. The lower temperatures are also suitable if contact times with the hot zone in a chamber are lengthened. Since this reaction is usually performed using an inert gas to promote the movement through the tube, this is readily obtainable. A simple reduction at the rate of flow of the carrier gas will increase the contact time.

When the thermal ring closure is conducted in a liquid phase, an inert solvent is utilized.

Within the context of this invention an inert solvent is defined as a solvent which can withstand the high reaction temperatures involved in the cyclization process without undergoing significant decomposition and which does not react with either the starting material or the product. Any high normal boiling point solvent fitting this criteria may be utilized as the inert solvent at atmospheric pressure. Lower normal boiling point solvents can be used if the reaction is conducted under pressure, i.e., in an autoclave, thereby attaining the desired temperature while preserving the solvent in the liquid phase. When the process is conducted in the liquid phase it is typically done so at a temperature of about 175° to 300° C., and preferably at about 200° to 250° C. The inert solvent must have a normal boiling point equal to or greater than the reaction temperature for the reaction to proceed at atmospheric pressure, or as already indicated if its normal boiling point is lower then the reaction must be conducted at supraatmospheric pressure. Examples of inert solvents are aromatic solvents including heteroaromatic and polycyclic aromatic solvents, alkylated aromatic solvents and halogenated aromatic solvents, saturated cyclic and acyclic hydrocarbons, organic esters including alkyl, phenyl and benzyl esters, and organic ethers including diphenyl ether, among others. More specific examples are methyl and t-butyl esters, decalin, 1-methylnaphthalene, naphthalene and biphenyl. Other suitable inert solvents may also be used including ketones, halogenated aliphatic hydrocarbons aliphatic esters and alcohols, among many others. Solvents which should be avoided since they are not within the above definition of an inert solvent include olefins, primary and secondary amines and carboxylic acids.

Typically, when the cyclization reaction is conducted in the liquid phase, the concentration of the enol ether or the ketal of the benzalacetone in the solvent may be varied over a broad range. Typically, the ketal or enol ether is present in an amount of about 0.01 moles to 1.0 moles per liter of the solvent.

Illustrative of suitable $R^2$ groups in the structures are methyl, ethyl, propyl, butyl, pentyl, hexyl, decyl and the like and examples of suitable $R^2$ groups in the ketal (I) when taken together are ethylene, trimethylene, tetramethylene and the like.

Exemplary of $R^3$ groups are hydrogen, halo such as chloro, bromo and fluoro; carboxy; alkyl such as described for $R^1$ and $R^2$; alkoxy such as methoxy, ethyoxy, propoxy, butoxy, pentoxy and the like; acyl such as ethanoyl, propanoyl, butanoyl, pentanoyl and the like; acyloxy such as ethanoyloxy, propanoyloxy, butanoyloxy, pentanoyloxy and the like; carbalkoxy such as methoxycarbonyl, ethyoxycarbonyl, propoxycarbonyl, butoxycarbonyl, etc.; alkylthio such as methylthio, ethylthio, propylthio, butylthio, pentylthio, etc.

Also, the aromatic ring of the benzalacetone may be substituted at any position, although preferred positions are the ortho and para positions of the ring with respect to the carboxy-containing residue. If the ring substitution is in either the para or ortho position, the products are entirely predictable. More specifically, para-substituted ketals or enol-ethers of the benzalacetone undergo ring closure to yield 6-substituted 2-acetonaphthones ortho-substituted alpha-acetyl benzalacetones yield 8-substituted, 3,4-dihydro 2-acetonaphthones. On the other hand, the meta-substitution of the aromatic ring of the benzalacetone leads to a mixture of the isomeric 5- and 7-methoxy substituted 2-acetonaphthones, e.g., with the latter predominating slightly in the case of the methyl m-methoxy acetyl benzalacetone ketal or enol ether.

Enol ethers of the acyl-substituted benzalacetones can be obtained by heating the related ketals at a temperature of about 25° to 300° C., preferably 75° to 250° C. and more preferably above 125° C. or by distilling the ketal.

In one particular embodiment of the invention, the heating step producing the cyclization of the ketal of an acyl-substituted benzalacetone is heated at the aforementioned temperatures to produce the related enol ether of the benzalacetone, and then the thus obtained enol ether of the acyl-substituted benzalacetone is heated at a temperature effective to cyclize said enol ether to form the substituted 2-acetonaphthones. When the cyclization of the enol ether of the acyl-substituted benzalacetone is conducted in the vapor phase, it is preferably done at a temperature of about 150° to 800° C., and more preferably about 350° to 600° C., and a pressure of about 0.001 mmHg to 3 atm, and more preferably about 0.1 mmHg to atmospheric pressure. However, much higher temperatures can also be used without difficulty, such as temperatures in excess of about 800° C. More commonly, the conditions under which the cyclization of the enol ether of the benzalacetone is conducted are similar to the conditions described above for the cyclization of the related ketal. It should be noted that the conversion of the ketal to the cyclic product proceeds through the formation of an enolic structure.

When the thermal ring closure of the enol ether benzalacetone is conducted in a liquid phase, an inert solvent is utilized. Typically, solvents as those described above for the similar reaction of the related ketal are also useful in this case. When the process is conducted in a liquid phase, it is preferably done at a temperature of about 175° to 300° C., and more preferably about 200° to 250° C. Similar conditions are also suitable for the cyclization of the enol ester of benzalacetone. Up to the present time the prior art has not addressed in general, or by means of examples, the ring closure of ketals of acyl-substituted benzalacetones to generate 2-acetonaphthones. Furthermore, not even instances of simpler benzalacetone ketals being used to generate a naphthalene are known.

In another aspect of the invention, the 2-acetonaphthones are prepared from an acyl-substituted benzalacetone of the formula defined above and a ketalizing agent, and the thus obtained ketal is then cyclized by heating as described.

A number of methods for the ketalization of ketones are known (Gasparrini, F., Giovannoli, M., and Misiti, D., Tetrahedron 40: 1491 (1984) and references cited therein). However, no known applications of these methods to acyl-substituted benzalacetones are known.

The ketal of the acyl-substituted benzalacetone may be obtained by reacting an acyl-substituted benzalacetone with a ketalizing agent. Suitable ketalizing agents are alkyl glycols and tri-alkyl orthoesters and preformed dialkyl ketals and acetals such as ($C_2$–$C_{12}$)-glycols, e.g., 1,2- or 1,3-glycols, ($C_1$–$C_{12}$)alkyl orthoformates and ($C_1$–$C_{12}$)dialkyl-ketals derived from ($C_1$–$C_{12}$)ketones. Examples of suitable glycols and orthoformates are neopentyl glycol, propanediol, 1,2- and 1,3-ethylene glycol, trimethyl orthoformate and the like. Preferred are alkyl glycols and alkyl orthoformates having 1 to 5 carbon atoms. Alkyl glycols and di- and tri-alkyl orthoformates are commercially available or may be prepared by methods known in the art which need not be described herein.

The reaction of the benzalacetone with a ketalizing agent is preferably conducted in the presence of an acidic catalyst at a temperature of about 25° to 250° C., and more preferably about 40° to 200° C. Typically, this reaction is conducted at atmospheric pressure. However, other pressures are also suitable.

Preferred acidic catalysts are strong acids such as sulfuric acid, trifluoroacetic acid, hydrochloric acid or sulfonic acid or an acidic resin such as an acid-exchange resin. Acidic resins are commercially available or can be prepared by methods known in the art which need not be described herein. A preferred acid resin is Amberlyst 15 ®.

In the reaction of the benzalacetone with the ketalizing agent may vary widely but ordinarily falls in the range of about 1:1 to 1:5 molar equivalents, preferably about 1:1 to 1:3 molar equivalents. The reaction temperatures employed are those sufficient to effect the ketalization reaction and normally fall in the range of about −25° to 250° C., preferably about 0° to 200° C. The reaction proceeds readily at atmospheric pressure but the reaction can be conducted under pressure if desired.

The ketalization reaction is generally conducted in a liquid phase and an inert solvent may be added. Within the context of this invention, an inert solvent is defined as a solvent which can withstand the reaction temperatures involved in the ketalization reaction without undergoing significant decomposition and without detracting from the formation of the product. High normal boiling point solvents may be utilized as the inert solvent at atmospheric pressure. Lower normal boiling point solvents can be used if the reaction is conducted under pressure, i.e., in an autoclave, thereby attaining the desired temperature while preserving the solvent in the liquid phase. The inert solvent must have a normal boiling point equal to or greater than the reaction temperature for the reaction to proceed at atmospheric pressure, or as already indicated if its boiling point is lower, the reaction must be conducted at supraatmospheric pressure. Examples of inert solvents are acyclic, cyclic and aromatic hydrocarbons, halides thereof or their azeotropes formed with water, alcohols and glycols from which the alkylene and alkyl residues of the $R^2$ substituents of the ketals are derived. A preferred group of solvents are alcohols or glycols such as methanol, ethanol and ethylene glycol.

The acetyl-substituted benzalacetones may be obtained by reacting acetylacetone (2,4-pentanedione) with a benzaldehyde substituted with $R^1$, wherein $R^1$ is as defined above. The Knoevenagel condensation of aromatic aldehydes and acetylacetone is a well known and efficient process for generating alpha-acetyl benzalacetones (Jones, Org. Reactions 15: 204 (1967), the content of which is incorporated herein by reference.)

In general, the reaction of the diketone with the benzaldehyde is conducted at a temperature of about −25° to 250° C., and more preferably about 25° to 150° C., and at a pressure of about 0.1 mmHg to 5 atm, preferably 1 atm. In this reaction, the diketone and the benzaldehyde are preferably present in a proportion of about 10:1 to 1:10, and more preferably about 1:1 to 2:1 by weight.

Cyclic ketals such as those generated by ketalizing with vicinal glycols are also useful in this process. These ketals are generally generated in the prior art by treating a ketone with an excess of the glycol in the presence of an acidic catalyst while water produced by the reaction is continuously removed.

The cyclization of the ketals or enol ethers of the invention to obtain 2-acetonaphthones proceeds with a crude yield of at least about 70 weight % to 85 weight % and the product is obtained with a purity greater than 80 weight % to 90 weight %.

The substituted 2-acetonaphthones may be purified by any of a number of standard methods, including chromatography, distillation or crystalization, among others. After purification, the yield of the substituted 2-naphthone based on the amount of starting benzalacetone is greater than about 40 mole % to 65 mole %, depending on the nature of the substituent on the aromatic ring of the starting acyl-substituted benzalacetone.

Having now generally described this invention, the same will be better understood by reference to certain specific examples, which are included herein for purposes of illustration only and are not intended to be limiting of the invention or any embodiment thereof, unless so specified.

EXAMPLES

In all the examples listed below the intermediate ketals are identified on the basis of their proton NMR, infrared (IR), and mass spectra including an exact mass for the molecular ion. The final 2-acetonaphthone products are identified on the basis of their proton NMR, IR, and mass spectra.

EXAMPLE 1

Generation of 6-Methyl 2-Acetonaphthone

A solution of 10.1 grams (0.050 moles) of p-methyl alpha-acetyl benzalacetone (IUPAC name: 3-(4-methylbenzylidene)-2,4-pentanedione) in 60 mL of 1/1 (vol/vol) trimethyl orthoformate/methanol was prepared and to this solution was added 2 to 2.2 grams of Amberlyst-15 ®. The reaction mixture was stirred at room temperature for 2.5 hours and the solution was filtered to remove the AMberlyst-15 ® resin. The solution was neutralized using an Amberlyst-21 ® resin and again filtered. The intermediate monoketal was isolated by solvent removal in vacuo (weight of product: 11.9 grams). The compound was characterized spectroscopically and used in the subsequent pyrolysis without further purification. (The infrared spectrum of the product has a single carbonyl band at 1697 cm(−1) vs. two bands at 1709 cm(−1) and 1655 cm(−1), which is strong evidence for the E-isomer of the ketal. Proton NMR agreed with the product assignment but GC-MS revealed the presence of the enol ether as an additional product.

A sample of this monoketal (9.16 grams) was pyrolyzed using a simple drip-type pyrolysis unit which consisted of a 1-inch diameter quartz tube, filled with 20 cm of fine chips, e.g., Vycor ® chips, and placed in a 12-inch electric furnace. A thermal couple was used to monitor temperature and a furnace was used to maintain the temperature between 475° to 495° C. The movement of the material through the tube is promoted by an inert gas purge (50 mL/hour) and the crude, liquid ketal was added at a rate of 2 mL/hour. The yield of 6-methyl 2-acetonaphthone after chromatographic purification was 4.67 grams (66% yield for the overall conversion of p-methyl alpha-acetyl benzalacetone to 6-methyl 2-acetonaphthone).

EXAMPLE 2

Generation of 2-Acetonaphthone

Following the procedure described in Example 1, alpha-acetyl benzalacetone was converted to 2-acetonaphthone in 64% yield.

EXAMPLE 3

Generation of 6-Chloro 2-Acetonaphthone

Following the procedure described in Example 1, p-chloro alpha-acetyl benzalacetone was converted to 6-chloro 2-acetonaphthone in 61% yield.

EXAMPLE 4

Generation of 6-Methylthio 2-Acetonaphthone

Following the procedure described in Example 1, p-methylthio alpha-acetyl benzalacetone was converted to 6-methylthio 2-acetonaphthone in 56% yield.

EXAMPLE 5

Generation of 6-Methoxy 2-Acetonaphthone

Following the procedure described in Example 1, p-methoxy alpha-acetyl benzalacetone was converted to 6-methoxy 2-acetonaphthone in 46% yield.

EXAMPLE 6

Generation of 6-Methoxy 2-Acetonaphthone in a Liquid Phase Process

The dimethyl ketal of p-methoxy alpha-cetyl benzalacetone was generated as in Example 5 and rather than using the vapor phase pyrolysis, the ketal was cyclized by dissolving 2.50 grams of the crude ketal in 50 mL of 1-methylnaphthalene (b.p. 240° to 241° C.).

The solution was maintained at reflux for 10 hours. The product was purified by removing the majority of the solvent using distillation under reduced pressure and then chromatographing the residue using first hexane (to remove residual solvent) and then with 5% ethyl acetate in hexane. This procedure gave 0.76 grams (40% yield) of the desired 6-methyoxy 2-acetonaphthone.

The invention now being fully described, it will be apparent to one of ordinary skill in the art that many changes and modifications can be made thereto without departing from the spirit or scope of the invention as set forth herein.

What is claimed is:

1. A process for preparing a 2-acetonaphthone of the formula

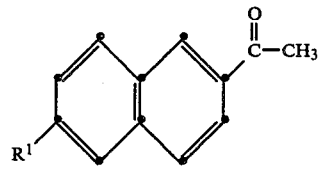

wherein $R^1$ is H, halo or ($C_1$–$C_{12}$)alkoxy, acyloxy, carboxy, carbalkoxy, acyl, alkyl or thioalkyl, said process comprising heating at a temperature within the range of 150° C. to 800° C. and a pressure within the range of about 0.1 mmHg to 3 atm a compound selected from the group consisting of a ketal of the formula

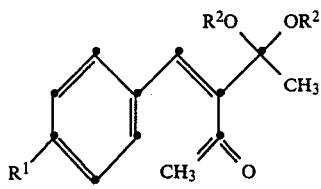

wherein $R^1$ is described above, and each $R^2$ is $(C_1-C_{12})$alkyl or the two $R^2$ taken together are $(C_2-C_{12})$alkylene, or an enol ether of the formula

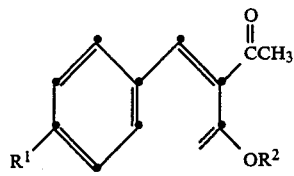

wherein $R^1$ is as defined above and $R^2$ is $(C_1-C_{12})$alkyl or $C_2-C_{12}$ acyl at a temperature effective to cyclize the compound and obtain said 2-acetonaphthones.

2. The process of claim 1, wherein the heating is conducted in the vapor phase.

3. The process of claim 1, wherein the temperature is about 350° to 600° C., and the pressure is about 0.1 mmHg to atmospheric pressure.

4. The process of claim 1, wherein the heating is conducted in the presence of a solvent at a temperature of about 175° to 300° C.

5. The process of claim 4, wherein the solvent has a normal boiling point which is higher than the same as the reaction temperature.

6. The process of claim 4, wherein the solvent has a normal boiling point which is lower than the reaction temperature; and the reaction is conducted under a pressure higher than about atmospheric pressure.

7. The process of claim 1, wherein the compounds heated is said ketal.

8. The process of claim 7, further comprising distilling the ketal prior to said heating step.

9. The process of claim 7, wherein the heating step is conducted by heating the ketal at a temperature of about 75° to 300° C. to obtain an enol ether of the benzalacetone; and then heating the enol ether at a temperature effective to cyclize said enol ether and obtain said 2-acetonaphthone.

10. The process of claim 9, wherein the heating of the enol ether is conducted in the vapor phase at a temperature of about 150° to 800° C.

11. The process of claim 10, wherein the temperature is about 350° to 600° C.

12. The process of claim 9, wherein the heating of the enol ether is conducted in an inert solvent at a temperature of about 175° to 300° C.

13. The process of claim 12, wherein the solvent has a normal boiling point which is higher than or the same as the reaction temperature.

14. The process of claim 12, wherein the solvent has a normal boiling point which is lower than about the reaction temperature; and the reaction is conducted under a pressure greater than about atmospheric pressure.

15. A process for preparing a 2-acetonaphthones of the formula

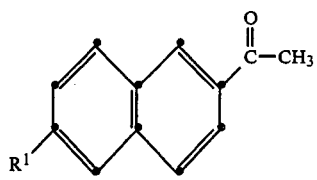

wherein $R^1$ is H, halo or $(C_1-C_{12})$alkoxy, acyloxy, carboxy, carbalkoxy, acyl, alkyl or thioalkyl, said process comprising reacting at a temperature in the range of $-25°$ to 250° C. an acyl-substituted benzalacetone of the formula

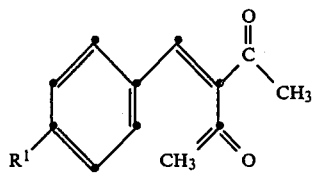

wherein $R^1$ is as defined above, with a ketalizing agent selected from the group consisting of alkyl glycols and di-alkyl acetals, di-alkyl ketals, and tri-alkyl orthoesters; said benzalacetone and said ketalizing agent being present in a proportion and under conditions effective to form a compound selected from the group consisting of a ketal of an acetyl-substituted benzalacetone of the formula

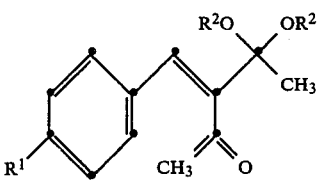

wherein $R^1$ is as defined above, and $R^2$ is $(C_1-C_{12})$alkyl or the two $R^2$ taken together are $(C_1-C_{12})$alkylene, or an enol ether of an acetyl-substituted benzalacetone of the formula

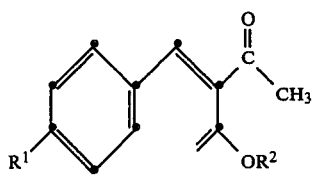

wherein $R^1$ is as defined above and $R^2$ is $(C_1-C_{12})$alkyl or $(C_2-C_{12})$acyl and heating said compound at a temperature effective to cyclize said compound and form said 2-acetonaphthone.

16. The process of claim 15, wherein the reaction of the benzalacetone with the ketalizing agent is conducted in the presence of an acid catalyst.

17. The process of claim 16, wherein the acid is an acidic resin.

18. A process for producing a 2-acetonaphthone of the formula

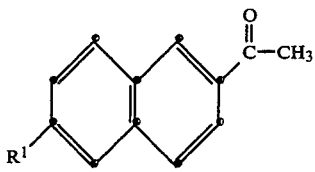

wherein $R^1$ is H, halo or $(C_1-C_{12})$alkoxy, acyloxy, carboxy, carbalkoxy, acyl, alkyl or thioalkyl, and $R^1$ is H, $(C_1-C_{12})$alkyl, $(C_6-C_{20})$aryl, $(C_7-C_{21})$alkaryl or araalkyl, said process comprising reacting at a temperature within the range of 350° C. to 600° C. and a pressure within the range of about 0.1 mmHg to atmospheric pressure acetylacetone with a benzaldehyde substituted with H, halo or, $(C_1-C_{12})$alkyl, carboxy, carbalkoxy, acyloxy, acyl, alkoxy or alkylthio; said diketone and said benzaldehyde being present in a proportion and under conditions effective to form an acyl-substituted benzalacetone of the formula

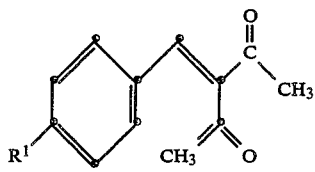

wherein $R^1$ is as defined above; reacting said benzalacetone with a ketalizing agent selected from the group consisting of alkyl glycols and di-alkyl acetals, di-alkyl ketals, and tri-alkyl orthoesters; said benzalacetone and said ketalizing agent being present in a proportion and under conditions effective to form a compound selected from the group consisting of a ketal of said benzalacetone of the formula

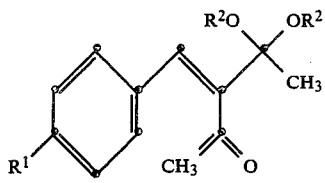

wherein $R^1$ is as defined above, and $R^2$ is $(C_1-C_{12})$alkyl or the two $R^2$ taken together are $(C_1-C_{12})$alkylene, or an enol ether of said benzalacetone of the formula

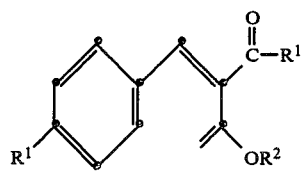

wherein $R^1$ is as defined above and $R^2$ is $(C_1-C_{12})$alkyl or $(C_2-C_{12})$acyl, and heating said compound at a temperature effective to cyclize said compound and form said 2-acetonaphthone.

* * * * *